United States Patent [19]
Michaelson

[11] Patent Number: 5,451,227
[45] Date of Patent: Sep. 19, 1995

[54] THIN FOOT PLATE MULTI BITE RONGEUR

[76] Inventor: Gary K. Michaelson, 438 Sherman Canal, Venice, Calif. 90291

[21] Appl. No.: 260,072

[22] Filed: Jun. 15, 1994

Related U.S. Application Data

[63] Continuation of Ser. No. 905,127, Jun. 24, 1992, abandoned, which is a continuation of Ser. No. 398,987, Aug. 28, 1989, abandoned, which is a continuation-in-part of Ser. No. 341,849, Apr. 24, 1989, Pat. No. 5,009,661.

[51] Int. Cl.⁶ .............................................. A61B 17/32
[52] U.S. Cl. ..................................... 606/83; 606/170; 606/205; 606/184
[58] Field of Search ............... 606/205, 206, 207, 83, 606/170, 167, 184, 79, 84, 171, 174; 128/753, 754, 751, 752

[56] References Cited

U.S. PATENT DOCUMENTS

| | | | |
|---|---|---|---|
| 2,984,241 | 5/1961 | Carlson | 606/84 |
| 3,752,161 | 8/1973 | Bent | 606/184 |
| 4,201,213 | 5/1980 | Townsend | 606/174 |
| 4,416,278 | 11/1983 | Miller | 606/184 X |
| 4,662,371 | 5/1987 | Whipple et al. | 604/22 X |
| 4,733,663 | 3/1988 | Farley | 606/83 |
| 4,777,948 | 10/1988 | Wright | 606/171 X |

FOREIGN PATENT DOCUMENTS 3709067  9/1988  Germany ............................. 606/205

*Primary Examiner*—Michael H. Thaler
*Attorney, Agent, or Firm*—Lewis Anten

[57] ABSTRACT

An improved bone biting rongeur with a thin foot plate, a replaceable hollow cutting slide storage member, capable of storing the cut bone, and a protective mechanism for protecting the foot plate is disclosed. The rongeur is capable of repeated and uninterrupted function, without removal from the surgical site and may be activated automatically by a power source.

18 Claims, 4 Drawing Sheets

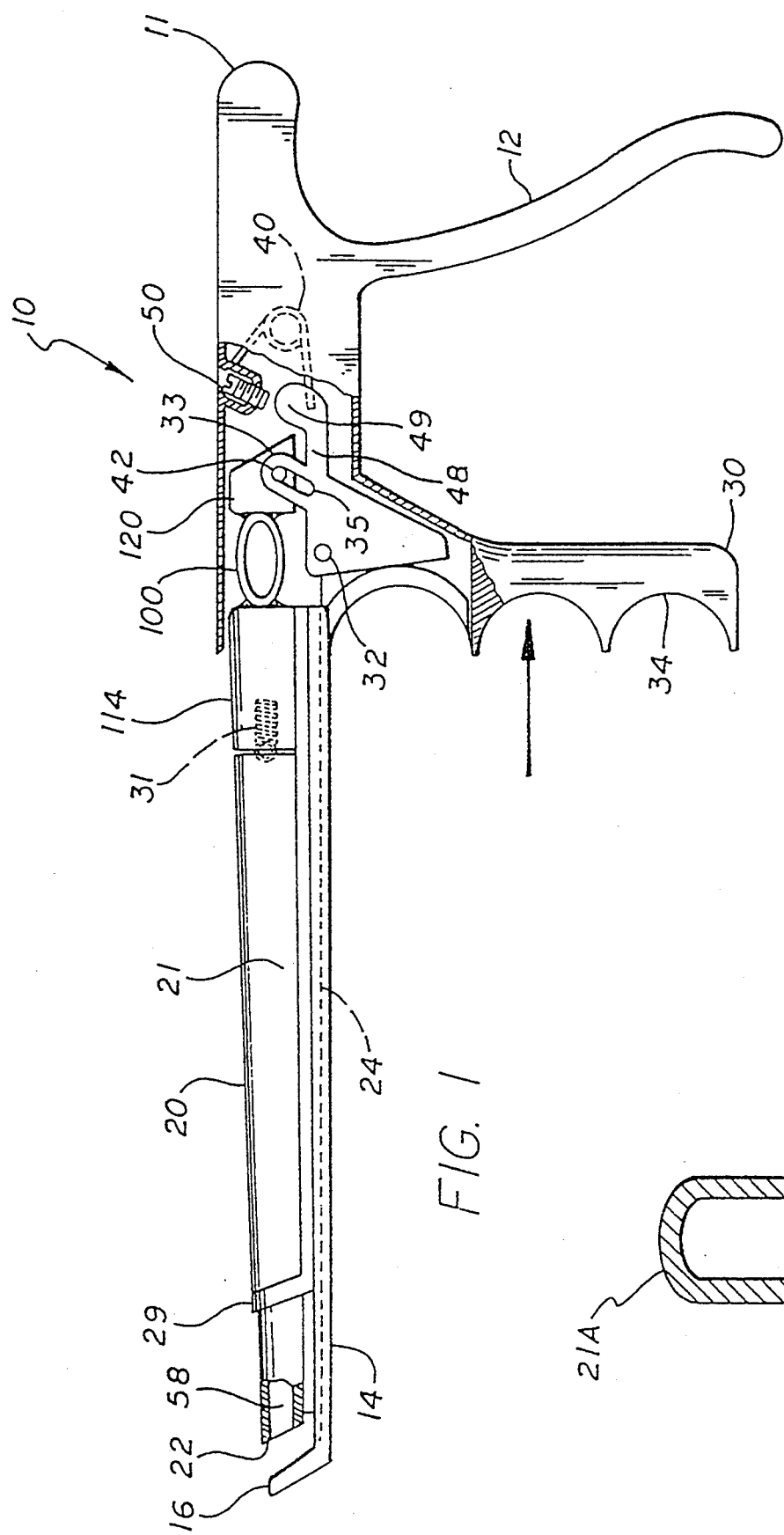
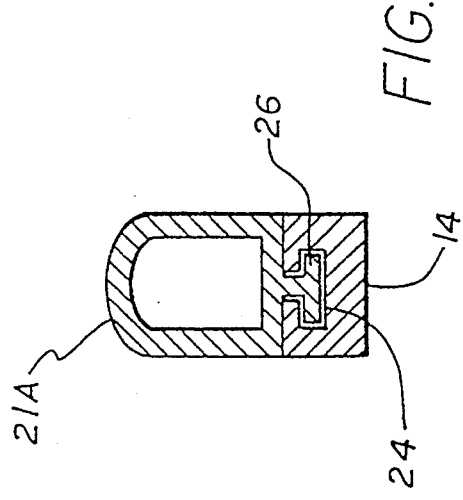
FIG. 1
FIG. 2

THIN FOOT PLATE MULTI BITE RONGEUR

RELATED APPLICATIONS

This application is a continuation of application Ser. No. 07/905,127, filed on Jun. 24, 1992, now abandoned, which is a continuation of application Ser. No. 07/398,987, filed on Aug. 28, 1989 now abandoned, which is a continuation-in-part of application Ser. No. 07/341,849, filed Apr. 24, 1989, now U.S. Pat. No. 5,009,661.

BACKGROUND

The present invention relates to surgical instruments for the purpose of biting bones and specifically to those of the Kerrison or similar type.

Kerrison type rongeurs are utilized in spinal surgery to remove the laminar bone from the posterior aspect of the spine and to thereby gain access into the spinal canal. The surgeon places the leading edge of the lamina within the open portion of the distal end of the Kerrison rongeur, and then by squeezing the handle causes the moving slide portion of the rongeur to be advanced through that portion of bone to the stationary foot plate thereby severing, or biting out, that portion of bone. The rongeur is then completely removed from the surgical site and passed to the scrub nurse for the removal from the instrument of that removed bone fragment.

To facilitate that necessary function, the foot plate is generally cupped, as is the cutting end of the moveable slide. If only the slide were cupped and the foot plate flat, then the bone would be so compacted into that singular cup as to make it nearly impossible to remove the fragment. However, because the foot plate portion of the Kerrison rongeur is below the lamina and proximate to the dural sac, spinal cord, and nerve roots, there is a compelling need to try to avoid any excessive thickness of the foot plate itself.

Therefore, the foot plate cup is generally not quite as deep as the slide cup and thus, even with the double cup design, the bone fragment tends to be compacted proximally, making its removal nevertheless somewhat difficult. The removal from the instrument of the bone fragment often requires that the nurse use a small rigid hook, or toothed forceps, and often further requires that the physician temporarily relinquish the instrument entirely to the nurse to make such bone removal possible. Once cleaned, the instrument is returned to the surgeon who in returning it to the surgical site must then reorient himself to the task at hand. This sequence must then be repeated over and over again with each bite of bone taken. Typically, such spinal procedures unfortunately require many such bites.

A consideration of the structure and function of the prior art rongeurs, and specifically in regard to the foot plate structure and its requisite thickness, is quite revealing. It would appear that in use the foot plate is subjected to five types of forces.

Consistent with its intended purpose, the foot plate is subjected to, and must withstand, that force necessary to actually cut through the bone, which we shall call the Bone Cutting Force. However, the surgeon has no way of knowing what that force is or even when he has reached or exceeded it. Accordingly, the foot plate is invariably exposed to a second force significantly greater than the Bone Cutting Force which we shall call the Terminal Squeezing Force. The Terminal Squeezing Force occurs after the bone fragment has been cut and is caused by the surgeon generating force in excess of the Bone Cutting Force. This results in the relatively massive slide portion of the instrument being driven with great mechanical advantage against the foot plate.

A third force encountered by the foot plate is a product of the fact that the instrument jaw generally opens to an extent greater than the combined depths of the cups such that the solid bony contents are physically crushed. This is the Bone Crushing Force, and again is additional to the Bone Cutting Force.

A fourth force that may impact upon the foot plate is that which occurs when the jaws of the rongeur encounter an object, which because of its physical structure, is unbiteable. In this situation, while the jaw is still in a relatively open position, again a force greater than the Bone Cutting Force is generated and in this case is then transmitted through the unbiteable object to the foot plate.

The fifth force to which the foot plate is subjected is leverage. When the jaws are not sufficiently sharp, or are worn such that they fail to completely close, then the bone will not be completely cut through, and the surgeon will rock the instrument back and forth to fracture through the remaining bony bridge. In this situation, the angle of the jaw in contact with the leading edge of the lamina becomes the fulcrum point. The foot plate, measuring generally less than one half of an inch in length, is one lever arm, while the remainder of the instrument through the shaft and handle is the other. Since these instruments generally measure on the order of 10 inches or so, the mechanical advantage, or force applied to the tip in a rocking maneuver is on the order of a magnitude of 20 to 1.

The ability to safely withstand repeated exposure to these five forces, and the previously discussed need to cup the innersurface of the foot plate, have in the past, determined the requisite thickness of the foot plate.

Since the prior art rongeurs required removal of the instrument after each cutting procedure, there was little, if any, benefit from use of a power source to operate the rongeur, as a single cutting operation was still all that could be achieved.

Reference is made to U.S. Pat. Nos. 4,722,338 to Wright et al. and 4,777,948 to Wright et al. 4,777,948 discloses a rongeur having a stationery hollow tubular cutting element 28 which may be removably attached to the rongeur. The entire assembly must be disengaged to replace the cutting element. Further, the device is not capable of being a multi bite rongeur, since only a short recess is provided for pulling the severed bone into the hollow cutting tube and the bone is then ejected after each cutting operation, as explained in U.S. Pat. No. 4,722,338 at Col.3, line 10. The collection of the cut bone is not achieved by the hollow cutting element. In fact, the cut specimen could fall into the wound, an unacceptable situation.

Further, in the Wright devices, attempted cutting of an unbiteable object will result in the breakage of a pin, as in existing conventional rongeurs, or breakage of the foot plate.

SUMMARY OF THE INVENTION

In the present invention a movable hollow slide member is pressed against a substantially flat foot plate of the rongeur by activation of the handle. The hollow slide member has cutting edges along the edges facing the foot plate. The present invention eliminates the requirements of the cupping of the foot plate which may now have only a raised cutting edge or may be generally flat. This results in the rongeured bone fragment being driven rearwardly where the movable slide portion of the rongeur has been deliberately relieved so as to facilitate that very phenomena. Thus, it is no longer necessary to retrieve the bone fragments by pulling them from the jaws during each operation of the rongeur. Since the cutting surface of the hollow slide member is hollow, rather than cupped, and if sufficient space is provided within the hollow slide member to accommodate additional removed bone fragments, then the instrument can be used repeatedly without the need to remove it from the wound after each bite to allow for cleaning. The introduction of each new bone fragment will serve to drive the prior bone fragments further proximally into the hollow slide member where they are collected and contained. The bitten bone is collected within the hollow slide member and is not allowed to simply pass through the instrument where it could become loose within the wound or lost as a surgical specimen.

Once the surgeon has completed use of the instrument, the bone which has been collected and contained can then be made available as a surgical specimen. The specimens can be removed by any means which would be obvious to one skilled in the art, such as by a pick or obdurator. The ability of the bone fragments to pass into the slide eliminates the bone crushing force noted above.

An adjustable internal protective stop mechanism allows the present invention to be adjusted so that the hollow slide member closes completely against the foot plate, and no further. This protective stop mechanism protects the foot plate of the present invention from the previously described Terminal Squeezing Force. The prior art rongeurs do not have such a stop in order to allow the manufacturer some freedom in assuring the complete closure of the jaws, and provide for the possibility of some increased clearance secondary to wear in the future, while still assuring complete jaw closure.

The present invention also embodies a foot plate protective spring mechanism comprising a spring body, which may be elastic, semi-elastic, hydraulic, or pneumatic, between the handle and the hollow slide member. The protective spring mechanism is relatively inelastic until subjected to forces in excess of the Bone Cutting Force. Beyond that point, the elastic behavior of the foot protecting member serves to reduce the force imparted to the foot plate. This serves to significantly mitigate the fourth force that encountered with engagement of an unbiteable object. The protective mechanism is not itself damaged by this function.

An alternative embodiment incorporates a torque limiting device, such as a pair of complementary splined surfaces held in opposition to one another, preferably by a cone shaped spring washer pressurized by an adjustable bolt with a nut, in place of the spring element 100. Such torque limiting device would be used in place of pivot pin 32. Once the permitted torque was exceeded, the two spine surfaces would slide relative to one another and prevent any additional torque. The device would be reset before use.

A further consideration is that only specific materials have proven serviceable for taking and holding an edge on surgical instruments. These materials have almost universally been of the martinsitic stainless steel series and generally of the type containing significant amounts of carbon in the form of carbide to provide for the requisite hardness. Much stronger materials acceptable for use in surgery, but unable to hold an edge, exist, such as MP35N "Elgiloy", "L605" cobalt chromium alloys and others. Eliminating the requirement of having a cutting edge on the foot plate makes it possible to make use of these stronger materials and to thereby again allow for an even greater reduction in the thickness of the foot plate.

The above features allow for a significant time savings to the surgeon and patient during use, as the instrument is thus capable of a multibite function, without the need to repeatedly remove the instrument from the surgical site. Further time savings, and greater patient safety, are also derived from obviating the need of the surgeon to constantly reorient himself during the operation.

Further, since the present invention makes multibiting feasible, there then exists a rationale for a power drive mechanism which can be constructed utilizing a self contained rechargeable battery pack or operated by a conventional electrical power supply for an activating mechanism. While powered rongeurs, including pneumatic powered rongeurs, have been used before, the requirement that the rongeur be removed from the wound after each use made such use impractical. The power drive mechanism of the present invention can be incorporated in a device similar to a hand held electrical stapler, having a solenoid activated drive responsive to the activation of a trigger. Such drive may have a "one shot" capability, where upon activation of the trigger the slide member is driven forward and automatically returned to its starting position. The trigger need only be released and activated again to perform another cutting procedure. The hollow slide member can be a replaceable disposable element, whereby the slide member may be removed, with its collected bone, after the operation. Each disposable hollow slide member would thus have a new sharp cutting edge.

OBJECTS OF THE PRESENT INVENTION

It is an object of the present invention to provide an improved rongeur which is easier to use;

It is another object of the present invention to provide an improved rongeur which is more reliable;

It is yet another object of the present invention to provide an improved rongeur which is stronger;

It is another object of the present invention to provide an improved rongeur which has a thinner foot plate;

It is still another object of the present invention to provide an improved rongeur which is less likely to break;

It is another object of the present invention to provide an improved rongeur which permits operations to be performed quicker, and with less danger.

It is still another object of the present invention to provide an improved rongeur capable of repeated biting action.

It is yet another object of the present invention to provide an improved powered rongeur.

These and other objects of the present invention will be evident from a review of the following specification and accompanying drawings.

BRIEF DESCRIPTION OF THE DRAWINGS

FIG. 1 is a side elevational view, partially broken away, of an improved bone rongeur constructed in accordance with the present invention.

FIG. 2 is a cross-sectional view of an alternative embodiment of the cutting portion of the rongeur of the present invention.

DETAILED DESCRIPTION OF THE PREFERRED EMBODIMENT

Figure 1A:
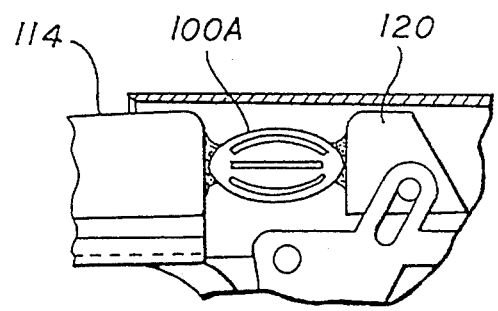
FIG. 1A is a side elevational view of an alternative embodiment of the elastic body of the rongeur of the present invention.
Figure 1B:
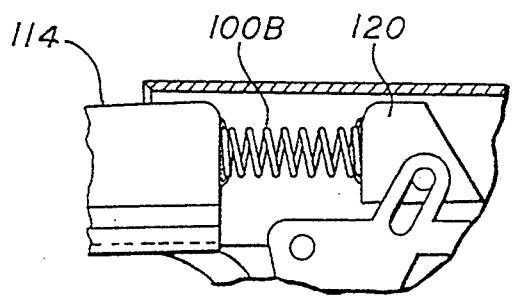
FIG. 1B is a side sectional view of an alternative embodiment of the elastic body of the rongeur of the present invention.
Figure 3:
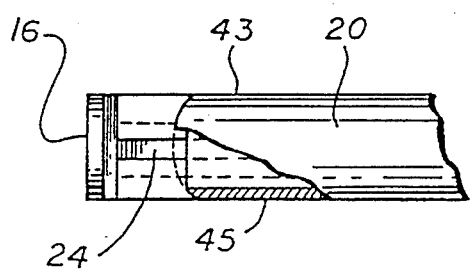
FIG. 3 is a top plan view, partially broken away, of the distal end of the rongeur of FIG. 1.

Referring now to FIG. 1, there is shown the bone rongeur constructed in accordance with present invention and consisting generally of a body 10 which has a rear handle 12 extending substantially perpendicularly about one inch from the rear end 11 of body 10 and extending distally about ten inches to form a long shaft 14 terminating at its distal end in a foot plate 16. A hollow slide assembly 20 has a cutting edge 22 at its distal end and is mounted on the shaft 14 for reciprocating movement on the shaft 14. Slide assembly 20 is slidably mounted to shaft 14 by a mounting means which in the preferred embodiment includes a slot 24 formed in the shaft 14 into which a complementary T-shaped runner 26 on the bottom of slide assembly 20 is fitted. Other means of attaching the slide assembly 20 to the shaft 14 may be employed.

Forward handle 30 pivotally attached by a pivot pin 32 to the body 10 serves as the activating means. The lower part of the forward handle 30 includes finger grip recesses 34 for the last three fingers of the hand, the second finger and thumb extending along the body as described in detail in the copending application Ser. No. 07/153,034, filed on Feb. 8, 1988, entitled MEDICAL INSTRUMENT HANDLE.

The upper part of the forward handle 30 has an extension 33 with an elongated opening 35 surrounding a pin 42 on slide drive extension member 120. A second extension 48 extends rearwardly from the upper part of the forward handle 30 to present an upward facing portion 49 within the body 10. An adjustable set screw 50, recessed within the body 10, is threaded through the body 10 to a position Just at the end of travel of the portion 49 of extension 48, thereby limiting the distal movement of the hollow slide assembly 20. Adjusting the locking set screw 50 controls and limits the distal movement of slide assembly 20.

The forward handle 30 is biased distally by coil spring 40, the coil spring 40 being attached at one end to the extension 48, and its other end to the body 10. Other spring mechanism, internal or external, and other biasing means, including pneumatic means, may be employed for urging the forward handle 30 distally.

Figure 4:
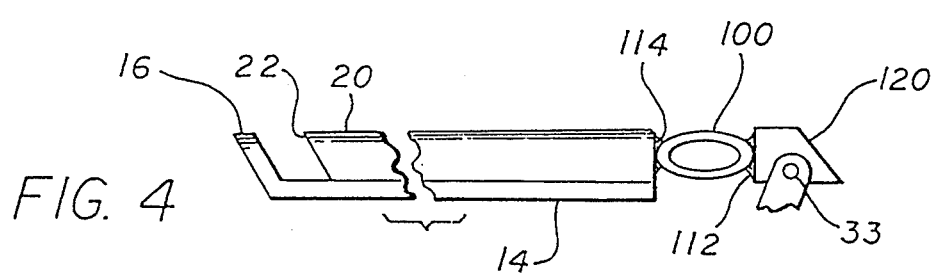
FIG. 4 is a partial side sectional view showing the protective spring mechanism.
Figure 5:
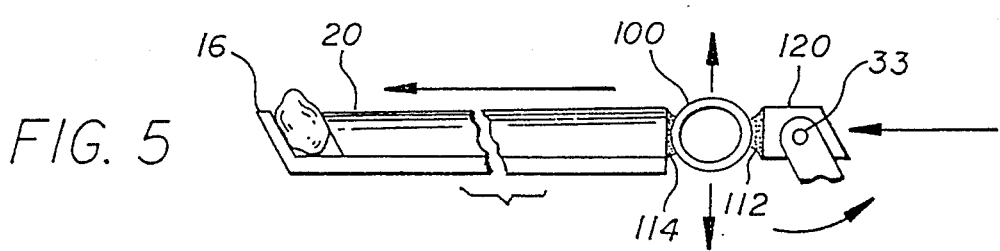
FIG. 5 is a partial side sectional view showing the protective mechanism distorted by an unbiteable object.

As shown in FIGS. 4 and 5 a protective safety mechanism 100 is shown for mitigating against greater than the Bone Cutting Force from being applied to the foot plate 16. The protective spring mechanism 100 is attached at one side 114 to the hollow slide assembly 20 and attached at its other side 112 to the slide drive extension member 120.

The protective safety mechanism 100 comprises a resilient elastic body, deformable along the axis of the shaft 24. Until the force on the resilient elastic body 100 exceeds a predetermined desired amount the resilient elastic spring 100 acts as a relatively solid member and the force is transmitted by the actuating handle of the device to the slide drive extension member 120, through the resilient elastic body 100 to the slide assembly 20. Once the force applied to the resilient spring body 100 exceeds the desired amount, such as when an unbiteable object is placed between the foot plate and the distal end of the slide assembly 20 as shown is FIG. 5, then the elastic body 100 is compressed thereby limiting the force applied to the foot plate 16. The resilient member, shown in FIGS. 4 and 5 is shown as an oval member, other equally available configurations can be employed, such as disclosed in the copending application. There include a spherical object, such as a hollow football shaped element 100A having slots shown in FIG. 1A, coil spring 100B shown in FIG. 1B, leaf springs solid compressible materials such as may readily be obtained, or any other element that is essentially, by the nature of its composition and/or configuration, relatively non elastic until a threshold force is applied. As indicated in application Ser. No. 341,849, now U.S. Pat. No. 5,009,661, the elastic member may be plastic.

Figure 7:
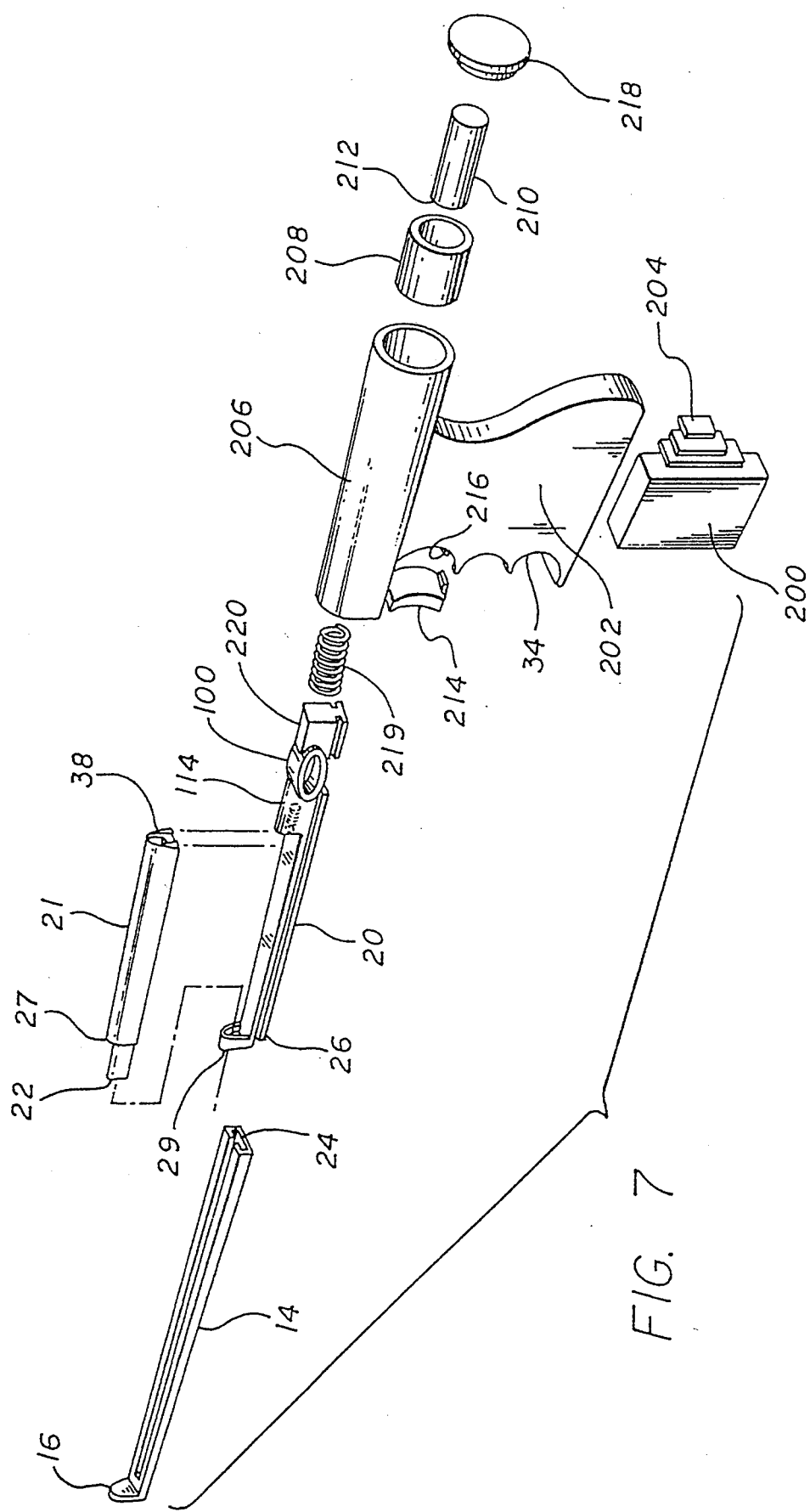
FIG. 7 is an exploded perspective view of the power rongeur of FIG. 6.

The foot plate 16 is shown in perspective in FIG. 7. While it may have a slight concave depression, it is to be understood that it is preferably substantially flat, with or without a cutting edge.

The distal end of the hollow slide assembly 20 opens into a recess 58 which is bounded by upper and side walls 43 and 45 sharpened to form cutting edges facing the foot plate 16. The bottom wall of slide member 20 is recessed from the foot plate for maximum bite since no cutting edge is required at the bottom wall. The recess 58 extends along the interior of the slide assembly 20 at least partially toward its proximal end. Preferably, the inside dimension of the chamber progressively increases from the distal end to the proximal end so that a number of successive bone fragments can slide into the chamber and stack up without jamming.

The hollow slide assembly 20, as shown in FIGS. 1 and 7 consists of a removable hollow cutting portion 21 which is tapered at its distal end 27 to fit below a guard member 29 on slide member 20. A spring loaded detent 31 in member 114 engages a recess 38 in the rear end of the removable hollow portion 21. The hollow cutting portion 21 may be attached in any number of conventional ways, such as cutting portion 21A shown in FIG. 2, by snap fit.

The use of a removable hollow cutting portion 21 permits a new sharp cutting edge to be provided for each operation. Both the chamber and the cutting edge could be made of metal or any other suitable material such as ceramic for the edge or a plastic (e.g. polycarbonate) for the chamber. A metal distal portion may be used as the floor of the chamber, the remainder of which may be clear polycarbonate. The chamber may be scored as to facilitate its being opened to allow ultimate specimen retrieval and to insure that the unit is not reused, thereby defending its purpose.

The rongeur of the present invention is used in the conventional manner to bite bone. The cut bone fragments are pushed by the foot plate 16, one by one, into a stack within the recess 58 of the removable slide member 21 after being cut and are not likely to fall back into the wound site because they are forced into the recess 58 with considerable force and because the size of the opening of the recess at the cutting edge 22 of the hollow slide member 21 increases away from the cutting edge 22. Thus it is not necessary that the cut bone fragments be removed during the surgical procedure, and bite after bite takes place, without the need to remove the rongeur from the wound.

In the present invention the set screw 50 is backed off and the forward handle 30 pulled rearwardly until the foot plate 16 of the instrument is in contact with the cutting edge 22 of the hollow slide member 21. The set screw 50 is then advanced until it just touches the flat portion 49. This assures that the instrument is closed completely, but no further, so that afterwards one can pull the handle 30 as hard as possible without damaging the foot plate 16, the force being borne on the set screw 50. This protects the foot plate 16 from the second detrimental force, the terminal squeezing force.

While the preferred embodiment of the present invention is a hand powered instrument, the use of alternative power sources such as electricity, battery supply, pneumatic, or other power sources can be employed.

In a powered rongeur the finger grip of the rongeur can then be devoted to turning on and off the power supply source to drive the instrument. If gas or other fluid is used, a pressure relief valve is preferably incorporated within the fluid line to establish a limit pressure, which may be set to the maximum desired biting force to be delivered.

Figure 6:
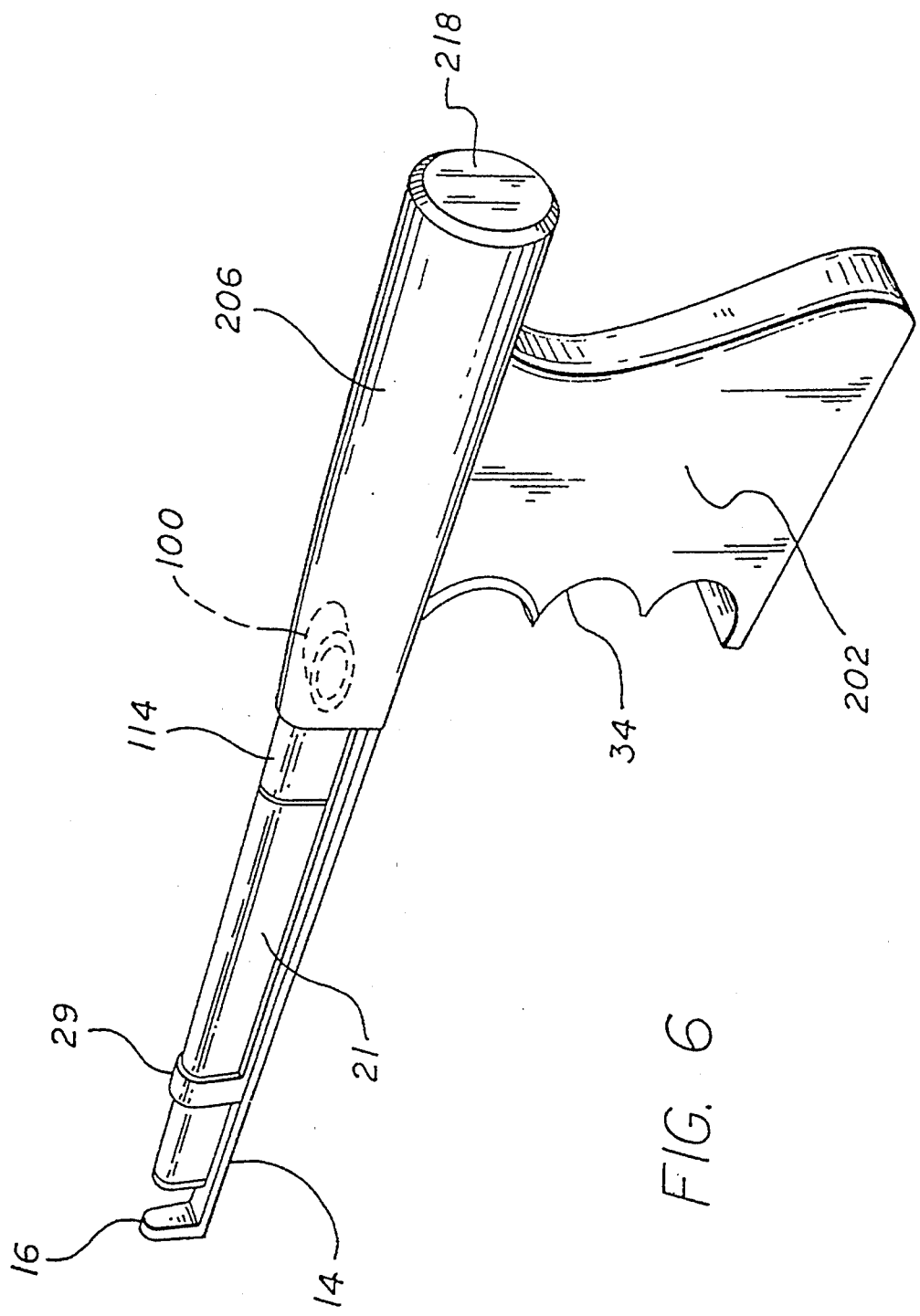
FIG. 6 is a perspective view of an embodiment showing a power rongeur.

Referring to FIGS. 6 and 7 a powered rongeur is shown. The space between the handles 202 is adapted for receipt of the electronic circuitry and the rechargeable battery pack 200. The battery pack makes contact at its poles at connections 204 located at the sides of the battery. A cover not shown holds the battery pack within the compartment.

Within the housing 206 above the handle a wire coil 208 surrounds a reciprocating drive member 210. The drive member is connected at one end 212 to spring 219 which has its other end connected to the drive extension member 220. The magnetic rod is spring biased by the strong spring 219 in the rearward direction. Whereby, upon activation of the trigger 214 which closes switch 216, the drive member 210 is driven forward driving the slide member 20 toward the foot plate 16.

The rear portion of the housing 206 can be opened for access to the compartment by removal of cap 218. Prior to sterilization, the cap 218 and the coil 208 can be removed from the housing 206. Pulling of the trigger 214 closes the switch 216 to cause one closing and opening of the rongeur 10. For a second closing operation, the trigger 214 must be released and then depressed again in order to close switch 216 once again.

The above device can be sterilized by heat upon removal of the coil and the battery pack. Alternatively, the device can be cold gas sterilized.

The drive member 210 can be adjustable along the longitudinal axis, either by threads or other means, so that it can be moved forward in the event that the foot plate 116 is to be sharpened. Also, a safety mechanism for preventing activation of the switch 216, well known in electrically operated devices, can be included. This could consist of a mechanical interference between the trigger and the switch to prevent activation of the switch 216.

In use, the surgeon would insert the rongeur 10 around the lamina to be cut and the trigger 214 would be pulled. The pulling of the trigger would cause the hollow slide assembly 20 to be driven forward closing, cutting the bone, and then automatically returned to the original open position. The speed of the driving element would result in additional cutting force, due to the momentum of the slide assembly 20. Releasing the trigger 214 would permit the jaws to open. The surgeon would then move the jaws, without removing the rongeur 10 from the wound, to a new area for biting the bone, again activating the trigger and causing the rongeur to close. The device could be programmed to close at a predetermined rate, so that it would automatically open and close. After completion of the cutting procedure the rongeur 10 would be removed and the hollow portion 21, removed and replaced.

Two solenoid coils can be used, a small one and a large one. The small solenoid would move the cutting member forward and after it is moved forward, the large one punches it, causing the cutting member to drive forward.

While the present invention has been described in association with the preferred embodiment, it is recognized that other variations of the present invention may be made without departing from the present invention.

Also, while the above solenoid activated medical instrument as been described in association with a rongeur, other medical instruments may be designed to incorporate such a mechanism.

What is claimed is:

1. A rongeur for cutting bone comprising a body; said body having a fixed shaft terminating in a foot plate; a slidable cutting assembly slidable in relationship to said shaft, said cutting assembly having engagement means for slidably engaging said shaft said cutting assembly including a cutting member having a longitudinal axis, said cutting member having a cutting means at its end proximate said foot plate, handle activation means associated with said body for moving said cutting assembly, a first spring for biasing said handle activation means, said first spring interposed between said body and said handle activation means, said cutting member having a hollow bone cutting collecting portion extending substantially the length of said cutting member and proximate said cutting means for collecting and storing bone therein from a number of bone cuttings; and a protective resilient member located along the longitudinal axis of said cutting member, said resilient member interposed between said cutting assembly and said handle activation means whereby force applied to said resilient member is transmitted to said slidable cutting assembly, said resilient member being compressed in a direction along said longitudinal axis.

2. The rongeur of claim 1 in which said rongeur has a stop means for limiting the distal movement of said slidable cutting assembly.

3. The rongeur of claim 2 in which said stop means is adjustable, for adjustably limiting the distal movement of said slidable cutting assembly.

4. The rongeur of claim 1 in which said foot plate is substantially flat.

5. The rongeur of claim 1 in which said cutting member is removably attached to the remainder of said cutting assembly.

6. The rongeur of claim wherein said resilient member is relatively incompressible when a predetermined amount of force is applied to said cutting member and compressible when force greater than the predetermined amount of force is applied to said cutting member.

7. The rongeur of claim 6 in which said resilient member comprises a deformable second spring means.

8. The rongeur of claim 7 in which said second spring acts as a relatively inelastic member until a threshold force is applied to said resilient member.

9. The rongeur of claim 1 including an electrically powered reciprocating device in which said slidable cutting assembly is responsive to said electrically powered reciprocating device.

10. The rongeur of claim 9 in which said electrical reciprocating device is battery powered.

11. The rongeur of claim 1 including solenoid activated means activated by a switch, said reciprocating device responsive to activation of said solenoid.

12. A rongeur for cutting bone comprising a body; said body having a shaft terminating in a foot plate; a cutting assembly movable in relationship to said shaft, said cutting assembly having engagement means for slidably engaging said shaft, said cutting assembly including a cutting member having a longitudinal axis, said cutting member having a cutting means at its end proximate said foot plate, handle activation means associated with said body for moving said cutting assembly relative said shaft, a first spring for biasing said handle activation means, said first spring interposed between said body and said handle activation means, and a protective resilient member located along the longitudinal axis of said cutting member, said resilient member interposed between said handle activation means and said cutting means, said resilient member being relatively incompressible when a predetermined amount of force is applied to said cutting assembly and compressible when force greater than the predetermined amount of force is applied to said cutting assembly, said resilient member being compressed in a direction along said longitudinal axis.

13. The rongeur of claim 12 in which said resilient member comprises a second spring.

14. The rongeur of claim 13 in which said second spring is a coil spring.

15. The rongeur of claim 12 in which said resilient member comprises a solid compressible member.

16. The rongeur of claim 15 in which said solid compressible member is made of plastic.

17. The rongeur of claim 12 in which said resilient member comprises an oval member said oval member being deformable upon excess force being applied to said oval member.

18. The rongeur of claim 17 in which said oval member is a football shape spheroid, said spheroid having slots therein for controlling the resiliency of said oval member.

* * * * *

UNITED STATES PATENT AND TRADEMARK OFFICE
CERTIFICATE OF CORRECTION

PATENT NO.     : 5,451,227
DATED          : September 19, 1995
INVENTOR(S)    : Gary K. Michelson, M.D.

It is certified that error appears in the above-identified patent and that said Letters Patent is hereby corrected as shown below:

<u>Title page,</u>
Item [12], change "Michaelson" to -- Michelson --.
Item [76], Inventor: change "Michaelson" to -- Michelson --.

Signed and Sealed this

Fourteenth Day of January, 2003

JAMES E. ROGAN
*Director of the United States Patent and Trademark Office*